(12) United States Patent
Lee et al.

(10) Patent No.: US 9,421,123 B2
(45) Date of Patent: Aug. 23, 2016

(54) PORTABLE COMBINED STIMULATION DEVICE FOR ALLEVIATING MENSTRUAL PAIN

(76) Inventors: Won joon Lee, Seoul (KR); Hyun jung Kim, Wonju-si (KR); Chang Sun Han, Incheon (KR); Shin won Kang, Yongin-si (KR)

( * ) Notice: Subject to any disclaimer, the term of this patent is extended or adjusted under 35 U.S.C. 154(b) by 676 days.

(21) Appl. No.: 13/121,683
(22) PCT Filed: Aug. 31, 2009
(86) PCT No.: PCT/KR2009/004887
§ 371 (c)(1),
(2), (4) Date: Jun. 13, 2011
(87) PCT Pub. No.: WO2010/035962
PCT Pub. Date: Apr. 1, 2010

(65) Prior Publication Data
US 2012/0109233 A1  May 3, 2012

(30) Foreign Application Priority Data
Sep. 29, 2008  (KR) .................. 10-2008-0095279

(51) Int. Cl.
*A61N 1/00* (2006.01)
*A61F 7/00* (2006.01)
(Continued)

(52) U.S. Cl.
CPC ............ *A61F 7/007* (2013.01); *A61N 1/36021* (2013.01); *A61F 2007/005* (2013.01);
(Continued)

(58) Field of Classification Search
CPC ............. A61N 1/00; A61N 1/02; A61N 1/08; A61N 1/18; A61N 1/28; A61N 1/375; A61N 1/378; A61F 7/00; A61F 7/02; A61F 7/03; A61F 7/08; A61F 7/112
See application file for complete search history.

(56) References Cited

U.S. PATENT DOCUMENTS

2002/0068960 A1* 6/2002 Saberski et al. ............... 607/46
2012/0221073 A1* 8/2012 Southwell et al. ............. 607/41

FOREIGN PATENT DOCUMENTS

JP  10-099363 A  4/1998
JP  2000-000259 A  1/2000
(Continued)

OTHER PUBLICATIONS

International Search Report for PCT/KR2009/004887 mailed May 10, 2010.
(Continued)

*Primary Examiner* — Christopher D Koharski
*Assistant Examiner* — Elizabeth K So
(74) *Attorney, Agent, or Firm* — AKC Patents, LLC; Aliki K. Collins

(57) ABSTRACT

A portable device for alleviating menstrual pain through transcutaneous electrical nerve stimulation (TENS) and thermal stimulation includes a transcutanous electrical nerve stimulating electrode pad and a planar heater embedded in the stimulating electrode pad. The stimulating electrode pad is a patch type one which is attachable/detachable to/from any body part with menstrual pain. The device further includes a power portion for supplying power to the menstrual pain alleviating unit, and an operation processing portion for generating a transcutaneous stimulating electrode control signal for controlling the transcutaneous stimulating electrode pad and a planar heater control signal for controlling the planar heater. The device further includes a temperature sensor mounted on the planar heater to sense the temperature of the planar heater, and an A/D converter for converting the signal output from the temperature sensor into a digital signal.

14 Claims, 7 Drawing Sheets

(51) Int. Cl.
   *A61N 1/36* (2006.01)
   *A61N 1/04* (2006.01)
(52) U.S. Cl.
   CPC . *A61F2007/0022* (2013.01); *A61F 2007/0027* (2013.01); *A61F 2007/0093* (2013.01); *A61F 2007/0096* (2013.01); *A61N 1/0456* (2013.01); *A61N 1/0484* (2013.01); *A61N 1/0492* (2013.01)

(56) References Cited

FOREIGN PATENT DOCUMENTS

| KR | 10-1993-0019233 | 10/1993 | | |
| KR | 20-0299458 | 12/2002 | | |
| KR | 10-2004-0085440 | 10/2004 | | |
| KR | 10-2007-0058389 | 6/2007 | | |
| KR | 1020080095279 B1 | 8/2009 | | |
| WO | WO 98/29063 | * | 7/1998 | A61F 7/03 |
| WO | WO2006006655 A1 | 1/2006 | | |

OTHER PUBLICATIONS

Written Opinion of the International Search Authority for PCT/KR2009/004887.

International Preliminary Report on Patentability for PCT/KR2009/004887.

* cited by examiner

PORTABLE COMBINED STIMULATION DEVICE FOR ALLEVIATING MENSTRUAL PAIN

RELATED APPLICATIONS

This application is a 371 application of International Application No. PCT/KR2009/004887, filed Aug. 31, 2009, which in turn claims priority from Korean Patent Application No. 10-2008-0095279, filed Sep. 29, 2008, each of which is incorporated herein by reference in its entirety.

TECHNICAL FIELD

The present invention relates to a portable combined stimulation device for alleviating menstrual pain using a Transcutaneous Electrical Nerve Stimulation (TENS) and a thermal stimulation, and in particular to a portable combined stimulation device for alleviating menstrual pain which makes it possible to provide abdominal and back areas with transcutaneous electrical nerve stimulation using a detachable stimulation electrode pad and to provide an abdominal area with a thermal stimulation using a planar heater installed in the stimulation electrode pad, thus alleviating menstrual pain, with the stimulation electrode pad being detachable to any portion where menstrual pain occurs.

BACKGROUND ART

Menstrual pain represents a pain occurring at a lower abdomen, a uterus, etc. during menstruation. The menstrual pain is subject to all women before menopause. Some of the women are even suffering from a lot pain, thus interfering with usual life. In case of menstrual pain, most women do usual life hoping that such pains calm down naturally or some women take a pain killer to alleviate pains. The alleviation of the pains using pain killer does not help alleviate the menstrual pain, thus causing some side effects due to the use of pain killer. The conventional warm heat fomenter developed to alleviate menstrual pain has some limits in place and time because it is not portable. The menstrual pain is subjected to interfering women at work as well as school class including various life behaviors, thus causing a lot of problems to women.

According to the traditional oriental medical field, the menstrual pain is called like menorrhalgia or abdomen pain during menstruation. As symptoms, women feel lower abdomen painful. There is extravasated blood due to aeremia and blood circulation. The menstrual pain is told that it is due to weak body system or the lack of blood due to surgical operation.

According to the Korean traditional therapy, the menstrual pains are alleviated by stimulating Kwan-wan acupuncture point and Seokmun acupuncture point of the lower abdomen using a moxa treatment and acupuncture.

FIG. 1 is a view for describing the Kwan-wan acupuncture point and the Seokmun acupuncture point. The Kwan-wan acupuncture point is positioned nine centimeter below navel, and the Seokmun acupuncture point is positioned six centimeter below navel. The Kwan-wan acupuncture point is generally called Danjun. When a patient feels fatigue or weakening energy, moxa treatment is good at such problems. The Kwan-wan acupuncture point corresponds to an acupuncture point, so it is related with the lack of energy of men as well as the enhancement of energy. The Kwan-wan acupuncture point can be stimulated to treat or cure uterus-related diseases, menstrual irregularity and leucorrhea. The Seokmun acupuncture point can be stimulated to treat or cure the symptoms that feces are stuck or menstruation does not come out, and gyneco-fluor disease and the uncontrolled urine paths after childbirth.

The TENS is directed to stimulating peripheral sensory nerves of skins by using current, thus alleviating pains via mechanical stimulations on the surrounding portions of pains like rubbing or massaging the surrounding portions of injuries or the pain portions. The TENS might be used to alleviate menstrual pains, not using chemical medicine. Non-steroidal anti-inflammatory drugs and oral contraceptive drugs are generally used for alleviating menstrual pains, which results in unsatisfied stimulations and side effects. The TENS has an advantage that it can be controlled by a user, not using a chemical medicine. The TENS is economical and is not dangerous, not having any limits when in use. It uses a low frequency and a lower level current.

In case of menstrual pains, the pains cover the abdomen and back areas while spreading over the areas of upper pubic, which can be alleviated by using the TENS.

The TENS is easy to use, but the standard device for the TENS has too big size for the use in actual life, and it cannot be easily used outdoor or at work or school.

It is urgently needed to develop a certain portable menstrual pain killer which provides TENS along with a thermal stimulation, thus alleviating menstrual pains.

DISCLOSURE OF INVENTION

Accordingly, it is an object of the present invention to provide a portable combined stimulation device for alleviating menstrual pain which makes it possible to alleviate menstrual pains with the aids of the thermal stimulation and TENS of the lower abdomen and the TES at the back portions.

It is another object of the present invention to provide a portable combined stimulation device for alleviating menstrual pain which is characterized in that abdomen and back portions are provided with TENS by using a detachable stimulation electrode pad, while providing a thermal stimulation at an abdomen with the aid of a planar heater installed in the stimulation electrode pad, thus alleviating menstrual pains, and a temperature senor is installed at a planar heater, so when the temperature of the planar heater is higher than a set level, the operation is stopped, thus enhancing safety.

It is further another object of the present invention to provide a portable combined stimulation device for alleviating menstrual pain which makes it possible to provide a TENS to an abdomen and back portions with the aid of a detachable stimulation electrode pad, thus alleviating menstrual pains.

It is still further another object of the present invention to provide a portable combined stimulation device for alleviating menstrual pain which makes it possible to provide thermal stimulations to a Kwan-wan acupuncture point and a Seokmun acupuncture point with the aid of a planar heater, thus alleviating menstrual pains.

It is still further another object of the present invention to provide a portable combined stimulation device for alleviating menstrual pain which makes it possible to save natural resource and to prevent ecological environment by using a rechargeable portable secondary battery, not a disposable type, and a USB charging unit and a charging operation at a chargeable cigar jack of a vehicle.

To achieve the above objects, there is provided a portable combined stimulation device for alleviating menstrual pains, comprising a transcutaneous stimulation electrode pad part which includes a transcutaneous stimulation electrode, thus providing an abdomen or a back portion with a transcutaneous stimulation; a planar heater part which includes a planar heater, thus providing a warm heat stimulation to an abdomen; a temperature sensing part which includes a temperature sensor, thus detecting the temperature of the planar heater part by engaging the temperature sensing part at the planar heater part; and a computation process part which controls the driving operations of the transcutaneous stimulation electrode pad part and the planar heater part and controls the driving of the planar heater part to stop when the temperature detected by the temperature sensing part is higher than a previously set temperature of the planar heater part.

To achieve the above objects, according to another embodiment of the present invention, there is provided a portable combined stimulation device for alleviating menstrual pain, which is directed to alleviating menstrual pains having a pain at a pubic area, comprising a menstrual pain alleviating part which includes a transcutaneous stimulation electrode pad part with a transcutaneous stimulation electrode for thereby providing an abdomen or a back portion with a transcutaneous stimulation, and a planar heater part with a planar heater for providing a warm heat stimulation to an abdomen; and a menstrual pain alleviating device body which includes a power part for supplying electric power to the menstrual pain alleviating part, and a computation process pat for generating a transcutaneous stimulation electrode control signal for controlling a transcutaneous stimulation electrode pad pat and a planar heater control signal for controlling the planar heater part.

It is characterized that the power part comprises a rechargeable battery.

It is characterized that the power part is charged by connecting a USB to a 220V commercial power, a notebook computer or a computer.

The battery of the power part is formed of a cellular phone battery and is rechargeable by using the cellular phone battery charger.

The menstrual pain alleviating part comprises a temperature sensing part which includes a temperature sensor and detects the temperature of the planar heater pat by engaging the temperature sensor at the planar heater body; and an A/D conversion part for converting an output signal from the temperature sensing part into a digital signal.

The computation process part allows the driving of the planar heater part to stop when the temperature detected by the temperature sensing part is higher than a previously set temperature of the planar heater part.

The menstrual pain alleviating part body comprises a key input part which includes an on/off switch of an operation of a menstrual pain alleviating device, a stimulation level setting mode part for setting the level of stimulation of the transcutaneous stimulation electrode pad part, a temperature setting mode part for setting the temperature of the planar heater, and an operation time setting mode part for setting the operation time of the transcutaneous stimulation electrode pad part and the planar heater; a display part which displays an output signal of the computation process part; and a D/A conversion part which converts an output signal from the computation process part into an analog signal.

There are further provided a transcutaneous stimulation electrode pad driving part which receives a transcutaneous stimulation electrode control signal from the computation process part via the D/A conversion part, thus driving the transcutaneous stimulation electrode pad; and a planar heater driving part which receives a planar heater control signal from the computation process part via the D/A conversion part, thus driving the planar heater part.

A driving signal for driving the transcutaneous stimulation electrode pad at the transcutaneous stimulation electrode pad uses a bipolar square wave of a frequency of 100~120 Hz.

When the temperature detected by the temperature sensing part is higher than a previously set temperature of the planar heater part, the state of which is informed by displaying or blinking a lamp or by using a vibrator to generate vibrations.

The transcutaneous stimulation electrode pad part is positioned to substantially cover the left and right sides of the front lateral collateral area and the anterior superior Iliac spine of the left and right sides of the pubic (upper) portion at the abdomen.

The transcutaneous stimulation electrode pad part is positioned to substantially cover the left and right sides of the back side including both lateral spinal cord portions of the spinal cord portion L3 of an inner side of a thigh and the spinal cord portion S2 level positioned at the perineum in the back portion.

The planar heater is positioned at an abdominal portion including the Kwan-wan acupuncture point and the Seokmum acupuncture point.

To achieve the above objects, according to further another embodiment of the present invention, there is provided a portable combined stimulation device for alleviating menstrual pain which includes a transcutaneous stimulation electrode pad part for providing a transcutaneous stimulation to an abdomen or a back, and a planar heater part for providing a warm heat stimulation to an abdomen, which comprises a circuit substrate part which includes a transcutaneous electrode circuit part at both left and right sides of the planar heater part for driving the transcutaneous stimulation electrode pad part, with the planar heater part being positioned at the center portion; a circuit housing upper cover part which is positioned on the circuit substrate part and acts like an upper cover for covering the circuit substrate part and includes a transcutaneous stimulation electrode pad engaging part which is formed at a portion above the transcutaneous stimulation electrode circuit part of the circuit substrate part for engaging the transcutaneous stimulation electrode pad part; a circuit housing lower cover part which is positioned below the circuit substrate part and acts like a lower cover for supporting the circuit substrate part and supports the circuit substrate part and is engaged with the circuit housing upper cover part; and an adhesion pad part which is fixed at an upper surface of the circuit housing upper cover part and is positioned on the transcutaneous stimulation electrode pad engaged at the transcutaneous stimulation electrode pad and comes into contact with the skin as a patch type pad formed of a conductive gel.

There is further provided a planar heater contacting part which corresponds to a center portion of the circuit housing upper cover part and is positioned at an upper side of the planar heater part of the circuit substrate part, thus transferring heat when coming into contact with skin.

The adhesion pad part is formed of a hydro gel with an adhesive property.

The transcutaneous stimulation electrode pad part is formed of a conductive rubber or a carbon electrode.

The circuit housing upper cover part and the circuit housing lower cover part are made of silicon.

A shoulder is formed at a rim of the adhesion pad engaging part allowing the adhesion pad part to be engaged to an upper surface of the circuit housing upper cover part, thus preventing the adhesion pad part to be pushed.

The transcutaneous stimulation electrode circuit part is printed with a conductive ink, and the transcutaneous stimulation electrode pad part becomes electrically conducted when coming into contact with the transcutaneous stimulation electrode circuit part, thus providing TENS.

A harness engaging part is formed at one side of the center portion of the circuit substrate part for connecting the signal lines of the transcutaneous stimulation electrode pad part and the planar heater part.

There is further provided a stomach warmer to which the menstrual pain alleviating part is engaged.

The stomach warmer includes a plurality of pockets into which left and right end portions of the menstrual pain alleviating part are fixedly inserted, with a ring being positioned at a center portion between neighboring pockets, with its upper and lower sides being closed, with its left and right sides being open, according to which the menstrual pain alleviating part is fixedly suspended over the ring.

Effects

In the present invention, it is possible to alleviate menstrual pains by providing thermal stimulation to a Kwan-wan acupuncture point and a Seokmun acupuncture point of a lower abdomen by using a planar heater.

The portable menstrual pain alleviating device according to the present invention makes it possible to provide thermal stimulation and a TENS to an abdominal area and back area at the same time or a separate time by using a planar heater, thus effectively alleviating menstrual pains.

The portable menstrual pain alleviating device according to the present invention is economical because a 3.7 voltages lithium ion battery usually used in a common cellular phone is used, and it can be charged using a common cellular phone charger or by connecting a USB to a notebook computer or a desktop computer, thus obtaining an easier charging operation without using a separate charger.

A user wears a potable menstrual pain alleviating device according to the present invention, and fixes the same by using a stomach warmer part, thus obtaining an easier wearing of a menstrual pain alleviating device along with an easier portability at any place and time, which allows most of women who are suffering from menstrual pains to feel good, thus enhancing the life standard of women while supporting women's social activities.

BRIEF DESCRIPTION OF THE DRAWINGS

The present invention will become better understood with reference to the accompanying drawings which are given only by way of illustration and thus are not limitative of the present invention, wherein.

MODES FOR CARRYING OUT THE INVENTION

The construction and operation of a portable menstrual pain alleviating device according to an embodiment of the present invention will be described with reference to the accompanying drawings.

Figure 1:
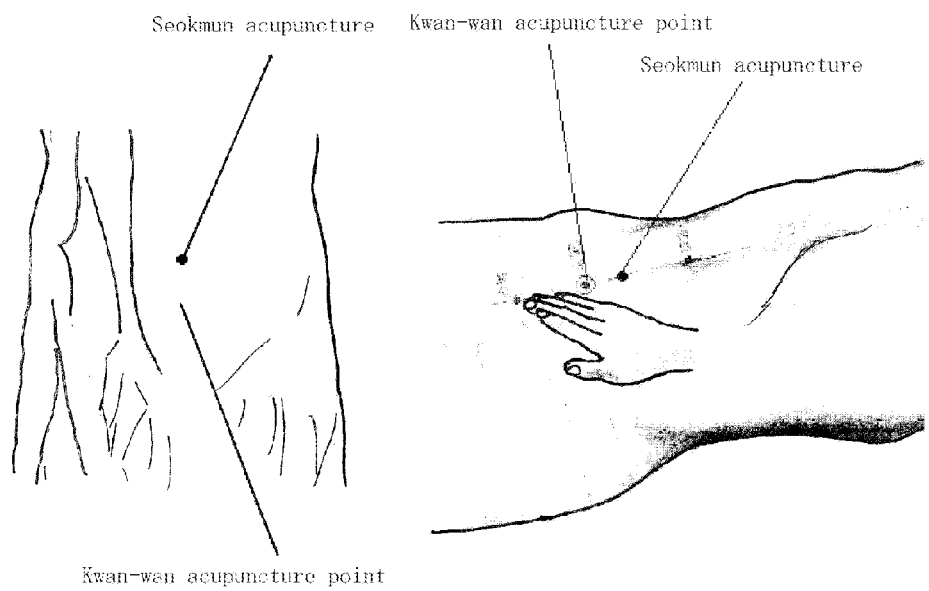
FIG. 1 is a view of a description of a Kwan-wan acupuncture point and a Seokmun acupuncture point.
Figure 2:
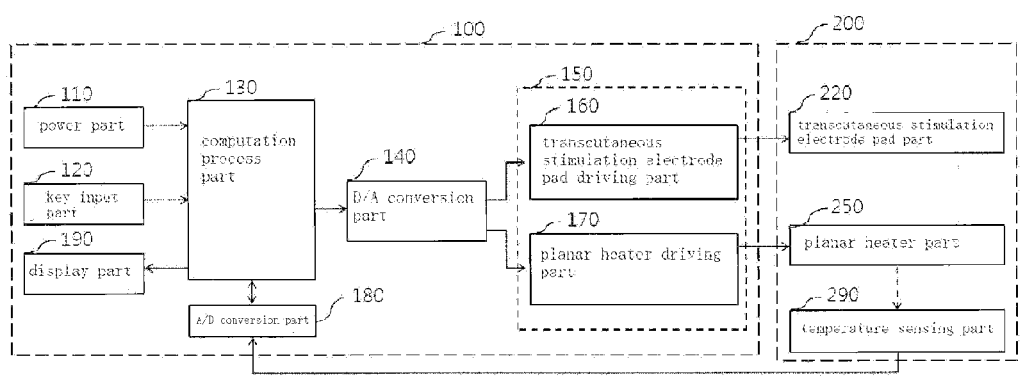
FIG. 2 is a block diagram illustrating a construction of a portable menstrual pain alleviating device according to an embodiment of the present invention.

FIG. 2 is a block diagram illustrating a construction of a portable menstrual pain alleviating device according to an embodiment of the present invention, which comprises a menstrual pain alleviating device body 100, and a menstrual pain alleviating part 200.

The menstrual pain alleviating body 100 is basically directed to generating a signal and a driving signal for controlling the menstrual pain alleviating part 200 by a user and comprises a power part 110, a key input part 120, a computation process part 130, a D/A conversion part 140, a driving part 150, an A/D conversion part 180 and a display part 190.

The power part 110 is a power supply means of a menstrual pain alleviating device and includes a battery part (not shown) for charging the battery for the use of an auxiliary power for a long time, and can be charged by connecting to a 220V commercial power, a notebook computer or a computer using a USB. In addition, the battery part (not shown) is a battery for a cellular phone and can be charged by a cellular phone battery charger by using a secondary 3.7V lithium ion battery which is most economical and efficient.

The key input part 120 is a means for setting the inputs for a control of the operation of the menstrual pain alleviating device and comprises a transcutaneous stimulation electrode pad on/off switch for determining whether or not to drive the transcutaneous stimulation electrode pad part 220 of the menstrual pain alleviating part 200, a planar heater on/off switch for determining whether or not to drive the planar heater part 250, a stimulation level setting mode part (not shown) for setting the stimulation level of the transcutaneous stimulation electrode pad part 220, a temperature setting mode part (not shown) for setting the temperature of the planar heater part 250, and an operation time setting mode part (not shown) for setting the operation time of the transcutaneous stimulation electrode pad part 220 and the planar heater part 250, respectively.

The computation process part 130 receives an output signal of the key input part 120 and stores the signals into a memory part and generates an output signal of the key input part 120, namely a control signal of the planar heater which controls the planar heater part 250 in accordance with a planar heater on/off signal and a temperature level set signal and generates a transcutaneous stimulation electrode control signal which controls the transcutaneous stimulation electrode pad part 220 in accordance with a transcutaneous stimulation electrode pad on/off signal and a stimulation level setting signal. In addition, the computation process part 130 receives a temperature signal detected by the planar heater part 250 from a temperature sensing part 290 via an A/D conversion part 180. When the temperature signal of the planar heater part 250 is higher than a temperature setting value of the planar heater part 250, the operation of the planar heater part 250 stops, thus preventing a low temperature burning damage due to the overheating of the planar heater part 250.

The D/A conversion part 140 is directed to converting an output signal of the computation process unit 130 into an analog signal.

Figure 4:
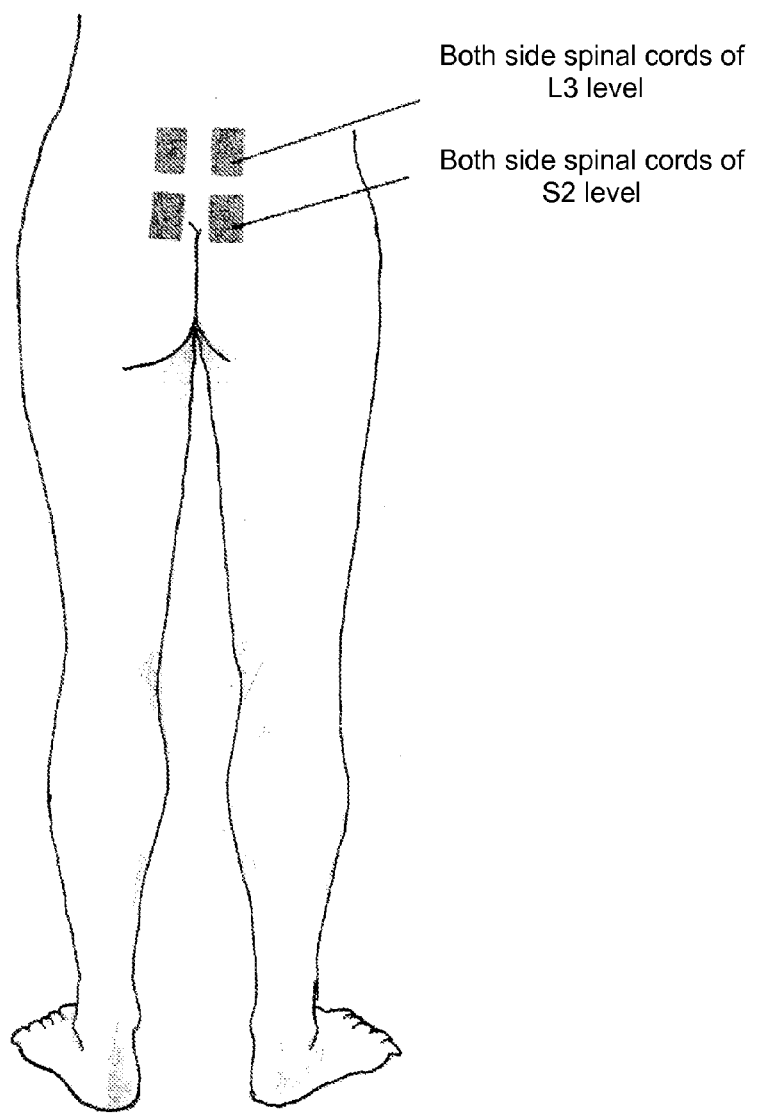
FIG. 4 is a view of a description of an example of the position of an electrode of a TENS for alleviating a pain occurring at a back portion due to a menstrual pain according to the present invention.

The driving part 150 receives a planar eater control signal and a transcutaneous stimulation electrode control signal from the computation process unit 130 via the D/A conversion unit 140, thus driving a transcutaneous stimulation electrode pad part 220 and a planar heater part 250, respectively. The driving part 150 comprises a transcutaneous stimulation electrode pad driving part 160, and a planar heater driving part 170. As shown in FIG. 4, the driving part 150 belongs to the menstrual pain alleviating device body 100, but according to a situation it might belong to the menstrual pain alleviating part 200, not to the menstrual pain alleviating device body 100.

The transcutaneous stimulation electrode pad driving part 160 is engaged to an abdomen for generating low frequency stimulations and receives a transcutaneous stimulation electrode control signal from the computation process part 130 via the D/A conversion part 140, thus driving the transcutaneous stimulation electrode pad part 220. The driving signal generated at the transcutaneous stimulation electrode pad driving part 160 has a bipolar square wave of a frequency of 100~120 Hz and a pulse width of 100~120 usec.

The planar heater driving part 170 is a means engaged to an abdomen for providing warm heat and receives a planar heater control signal from the computation process unit 130 via the D/A conversion part 140, thus driving the planar heater part 250.

The A/D conversion part 180 receives a planar heater temperature signal from the temperature sending part 290, which has sensed the temperature of the planar heater part 250, thus converting into a digital signal.

The display part 190 is a means for displaying an output signal of the computation process unit 130 and is composed of a printer, a display, etc. The display unit 190 receives a setting signal from the computation process part 130 and a temperature signal sensed by the temperature sensing part 290, thus displaying on a LCD screen of a display or a display means of the printer. When the planar heater part 250 has a temperature higher than the set temperature, a lamp might be controlled to blink or a vibrator (not shown) might be controlled to vibrate so that it is informed that the planar heater part 250 has a temperature higher than the set temperature.

The menstrual pain alleviating part 200 comes into direct contact with the skin and is driven in accordance with a driving signal from the menstrual pain alleviating device body 100 and comprises a transcutaneous stimulation electrode pad part 220, a planar heater part 250 and a temperature sensing part 290.

The transcutaneous stimulation electrode pad part 220 is a means driven by a diving signal of the transcutaneous stimulation electrode pad driving part 160 and comes into contact with an abdomen or back of a user, thus providing a transcutaneous stimulation signal in accordance with a driving signal.

The transcutaneous stimulation electrode pad part 220 might be attached to the abdomen covering the front lateral collateral area of the left and right sides of the pubic area (upper) in the abdomen (or the front lateral collateral area of the pain portion of the left and right side in the lower side) and the left and right sides of the anterior superior Iliac spine.

The transcutaneous stimulation electrode pad part 220 might be attached to the back portion covering the left and right sides of the back including both side spines of the spinal cord portion L3 positioned at the inner side of the thigh and the spinal cord S2 level positioned at the perineum.

The number of the transcutaneous stimulation electrode pad part 220 might be freely determined by a user, and the stimulation positions of the transcutaneous stimulation electrode pad part 220 might be freely changed by a user.

The planar heater part 250 is a means driven by means of the planar heater driving part 170 and provides a thermal stimulation in accordance with a driving signal while coming into contact with a user's abdomen. When the planar heat part 250 provides a thermal stimulation to the abdomen, the thermal stimulations can be provided over the abdomen portions including the Kwan-wan acupuncture points and the Seokmun acupuncture points, and the planar heater part 250 has a certain size enough to stimulate the Kwan-wan acupuncture points and the Seokmun acupuncture points, respectively. The stimulation positions of the planar heater part 250 might be freely changed by a user.

The temperature sensing part 290 is a means for detecting the temperature of the planar heater part 250 using a temperature sensor by engaging the same at the planar hearer part 250.

Figure 3:
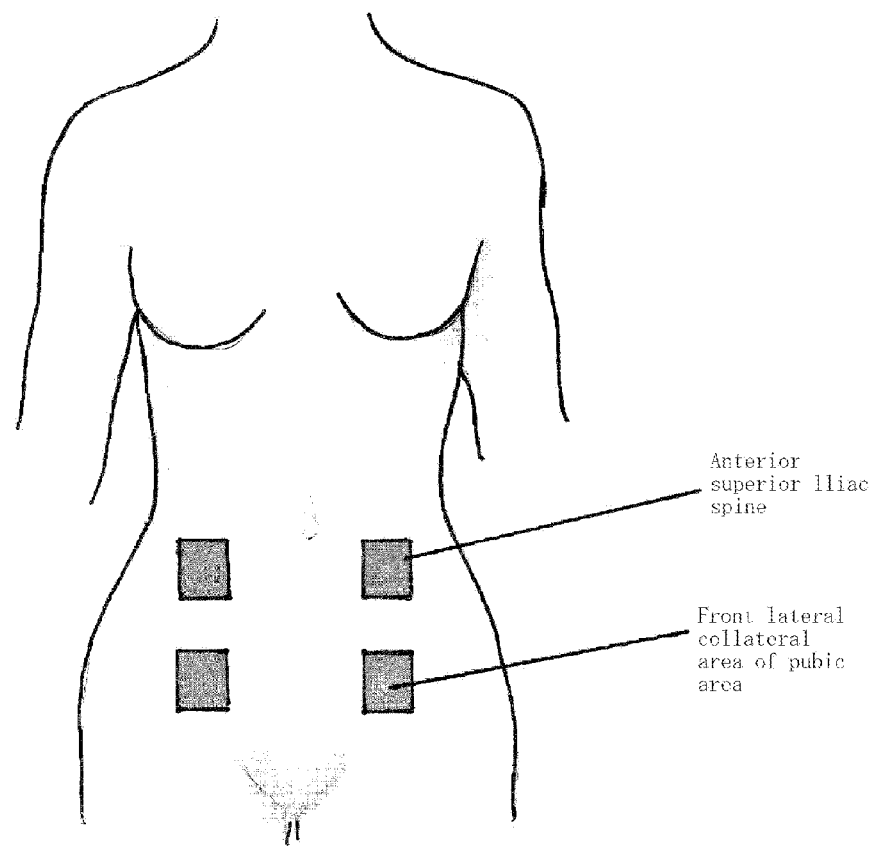
FIG. 3 is a view of a description of an example of the position of an electrode of a TENS for alleviating a pain occurring at an upper pubic area due to a menstrual pain according to the present invention.

FIG. 3 is a view for describing an example of the electrode position of the TENS so as to alleviate the pains spreading in the pubic upper regions due to menstrual pains.

In order to alleviate the pains in the pubic upper regions, the transcutaneous stimulation electrode pad part 220 might be attached to the abdomen covering the front lateral collateral area of the left and right sides of the pubic area (upper) in the abdomen (or the front lateral collateral area of the pain portion of the left and right side in the lower side) and the left and right sides of the anterior superior Iliac spine.

FIG. 4 is a view of a description for describing an electrode position of a TENS so as to alleviate the pains spreading in a back portion due to menstrual pains.

In order to alleviate the pans in the back portion, the transcutaneous stimulation electrode pad part 220 might be attached to the back portion covering the left and right sides of the back including both side spines of the spinal cord portion L3 positioned at the inner side of the thigh and the spinal cord S2 level positioned at the perineum.

Figure 5:
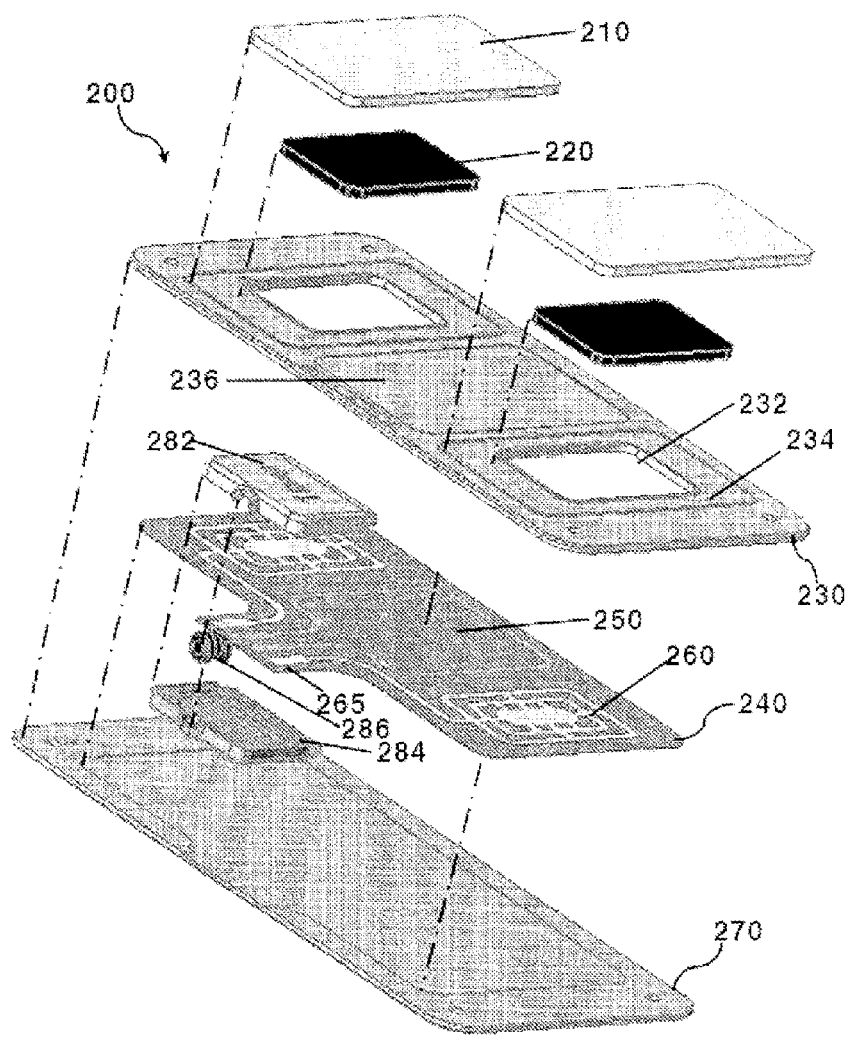
FIG. 5 is a disassembled perspective view of a menstrual pain alleviating part for a description of a menstrual pain alleviating part of a portable menstrual pain alleviating device according to a preferred embodiment of the present invention.
Figure 6:
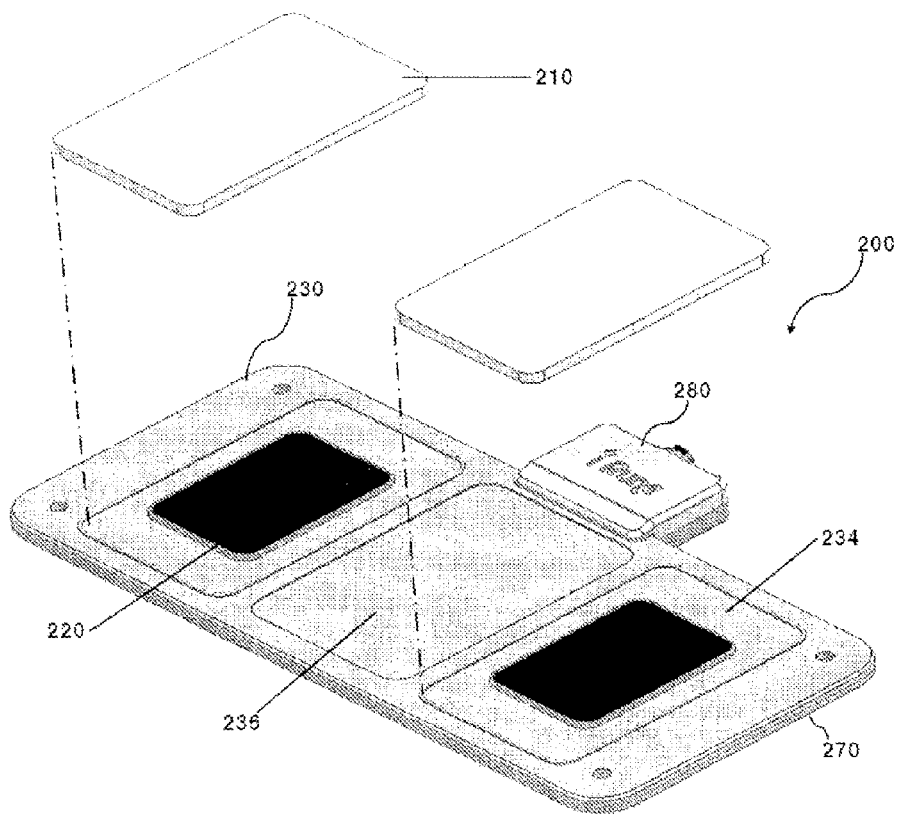
FIG. 6 is a view of a use description of a menstrual pain alleviating part of a portable menstrual pain alleviating device of FIG. 5.

FIG. 5 is a disassembled perspective view of a menstrual pain alleviating part for a description of a menstrual pain alleviating part of a portable menstrual pain alleviating device according to a preferred embodiment of the present invention, and FIG. 6 is a view of a use description of a menstrual pain alleviating part of a portable menstrual pain alleviating device of FIG. 5. The menstrual alleviating part 200 comprises an adhesion pad part 210, a transcutaneous stimulation electrode pad part 220, a circuit housing upper cover part 230, a circuit substrate part 240, a circuit housing lower cover part 270 and a harness part 280.

The adhesion pad part 210 is a patch type pad formed of a conductive gel while coming into direct contact with the skin and makes the skin and the transcutaneous stimulation electrode pad part 220 conductive with each other, thus facilitating an easier TENS, while assisting the fixing of the electrode at the skin. Namely, the adhesion pad part 210 is positioned between the skin and the transcutaneous stimulation electrode pad part 220, which helps fix the electrode in a detachable manner while providing electrolyte between the electrode and the skin, thus omitting the process of applying electrolyte and obtaining an easier exchange of the same. The adhesion pad part 210 is formed of an adhesive and exchangeable type hydro gel. The number and the position of the adhesion pad part 210 can be freely changed.

The transcutaneous stimulation electrode pad part 220 is a flexible electrode pad which is positioned at a lower side of the adhesion pad part 210 and comes into contact with the adhesion pad part 210 and is smaller than the adhesion pad part 210 in their sizes, with the transcutaneous stimulation electrode pad being formed in a thin plate and rod shape for obtaining a better contact performance to the curved portions of a human body with less influences from movements. The transcutaneous stimulation electrode pad part 220 might be formed of a flexible conductive rubber, and the transcutaneous stimulation electrode pad part 220 might be formed of a carbon electrode.

The transcutaneous stimulation electrode pad part 220 has a certain size enough to stimulate the front lateral collateral area of the left and right sides of the pubic (upper) portion in the abdomen and the anterior superior Iliac spin (upper side) of the left and right sides, and the transcutaneous stimulation electrode pad part 220 has a certain size enough to stimulate the spinal cord portion L3 positioned at the inner side of the thigh in the back region and the spinal cord portion of both sides of the spinal cord portion S2 positioned at the perineum.

The circuit housing upper cover part 230 is an upper cover of the housing of the circuit substrate part 240, with the adhesion pad part 210 and the transcutaneous stimulation electrode pad part 220 being engaged at the upper surface of the circuit housing upper cover part. The circuit housing upper cover part 230 is made of silicon material which gives an easier bending. The circuit housing upper cover part 230 comprises a transcutaneous stimulation electrode pad engaging part 232, an adhesion pad engaging par 234, and a planar heater contact part 236.

The transcutaneous stimulation electrode pad engaging part 232 is where portion wherein the transcutaneous stimulation electrode pad part 220 is engaged and is formed of a hole for receiving the transcutaneous stimulation electrode pad part 220, while helping the transcutaneous stimulation electrode pad part 220 be tightly engaged. The shapes and numbers of the transcutaneous stimulation electrode pad engaging part 232 are determined the shapes and numbers of the transcutaneous stimulation electrode pad part 220. The transcutaneous stimulation electrode pad part 220 might be provided in multiple numbers, so the transcutaneous stimulation electrode pad engaging part 232 might be provided in multiple numbers on the circuit housing upper cover part 230.

The adhesion pad engaging part 234 is where the adhesion pad part 210 is engaged, namely, is an adhering surface where the adhesion pad part 210 can be adhered to an upper side of the circuit housing upper cover part 230. Namely, the adhesion pad engaging part 234 includes a transcutaneous stimulation electrode pad engaging part 232 by which the transcutaneous stimulation electrode pad part 220 is engage on the circuit housing upper cover part 230, and then the adhesion pad part 210 is engaged on the resultant construction. The surface (upper surface) of the circuit housing upper cover part 230 comes into contact with the adhesion pad part 210.

The rim of the adhesion pad engaging part 234 is equipped with a shoulder. With the above shoulder portion, it is possible to stably fix the adhesion pad part 210 to the adhesion pad engaging part 234 with the aid of the shoulder portion of the rim of the adhesion pad engaging part 234 after the adhesion pad part 210 is adhered to the adhesion pad engaging part 234, while preventing the adhesion pad part 210 from being pushed backward when coming into contact with the skin. The shapes and numbers of the adhesion pad engaging part 234 can be changed depending on the shapes and number of the adhesion pad parts. The number of the adhesion pad engaging part 234 is the same as the number of the transcutaneous stimulation electrode pad engaging part 232.

The planar heater contact part 236 comes into contact with the user's skin and the planar heater part 250 at its lower side, thus transferring a thermal stimulation from the planar heater part 250 to the skin. Namely, at the lower side of the circuit housing upper cover part 230 is provided the planar heater part 250, and the planar heater contact part 236 is provided on the circuit housing upper cover part 230 of the upper side of the planar heater part 250, thus transferring the warm heat from the planar heater part 250 to the skin. The shapes and sizes of the planar heater contact part 236 might be changed depending on the shapes and sizes of the planar heater part 250. It is preferred that the planar heater contact part 236 is made of a thermally conductive material.

The circuit substrate part 240 is supported between the circuit housing upper cover part 230 and the circuit housing lower cover part 270. Namely, the circuit substrate part 230 is positioned at a lower side of the circuit housing upper cover part 230 and is smaller than the circuit housing upper cover part 230 in their sizes. There are a planar heater part 250, a transcutaneous electrode circuit part 260 and a harness engaging part 265 as means for driving the transcutaneous stimulation electrode pad part 220 and the planar heater part 250.

The planar heater part 250 is positioned at a center portion of the circuit substrate part 240 while providing thermal stimulation at the abdomen including the Kwan-wan acupuncture points and the Seok-mum acupuncture points when coming into contact with the skin and has a certain size enough to stimulate the Kwan-wan acupuncture points and the Seok-mum acupuncture points, respectively. The stimulation positions of the planar heater part 250 might be freely changed by a user. The planar heater part 250 might be formed in a film type and might be formed of a flexible thin material.

The transcutaneous electrode circuit part 260 is a circuit for driving the transcutaneous stimulation electrode pad part 220, thus providing TENS as the transcutaneous stimulation electrode pad part 220 becomes electrically conducted when the transcutaneous electrode circuit part 260 comes into contact with the lower side of the transcutaneous stimulation electrode pad part 220. The transcutaneous electrode circuit part 260 is a portion printed with a conductive ink on the circuit substrate part 240, namely, is a means for providing the TENS as it comes into contact with a lower surface of the transcutaneous stimulation electrode pad part 220, and the transcutaneous stimulation electrode pad part 220 becomes electrically conducted. The positions, sizes and numbers of the transcutaneous electrode circuit part 260 can be freely changed depending on the positions, sizes, and numbers of the transcutaneous electrode circuit part 260.

The harness engaging part 265 is formed in a shape outwardly protruded from the circuit substrate part 240 and is used as a method for an engagement with the harness part 280, thus allowing the signal lines of the transcutaneous stimulation electrode pad part 220 and the planar hater part 250 to be connected to the harness part 280, and then the menstrual pan alleviating device body 100 is connected via the harness part 280.

The circuit housing lower cover part 270 is positioned at a lower side of the circuit substrate part 240 and is larger than the circuit substrate part 240 and is sized same as the circuit housing upper cover part 230 and is flexible because it is made of a silicon material.

The harness part 280 is a means for connecting a cable to the menstrual pain alleviating part 200, according to which the circuit housing upper cover part 230, the circuit substrate part 240 and the circuit housing lower cover part 270 are engaged, and then the harness part 280 is connected to a portion of the harness engaging part 265 of the circuit substrate part 240. Here, the harness part 280 comprises a first harness part 282 to be engaged with part of the circuit housing upper cover part 230, a second harness part 284 to be engaged with part of the circuit housing lower cover part 270, and a cable connection part 286 which is a passage to be connected with a cable.

As shown in FIG. 5, the planar heater part 250 is positioned at a center portion, and the transcutaneous stimulation electrode pad part 220 is positioned at both left and right sides. The positions and the numbers of the planar heater part 250 and the transcutaneous stimulation electrode pad part 220 are not limited thereto.

Figure 7:
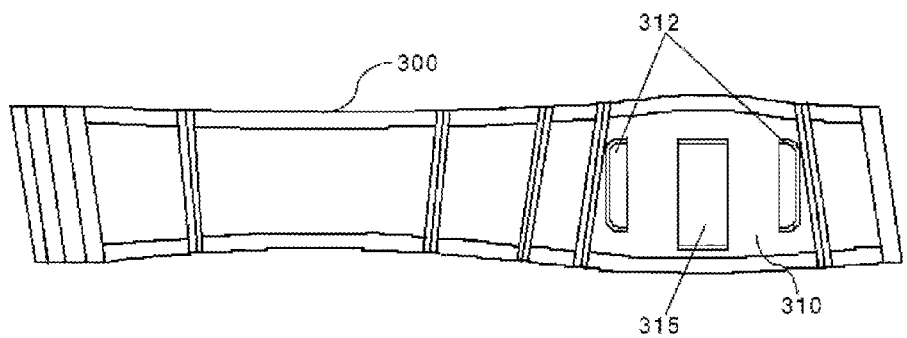
FIG. 7 is a rear side view of a stomach warmer part before a menstrual pain alleviating device is worn according to an embodiment of the present invention.
Figure 8:
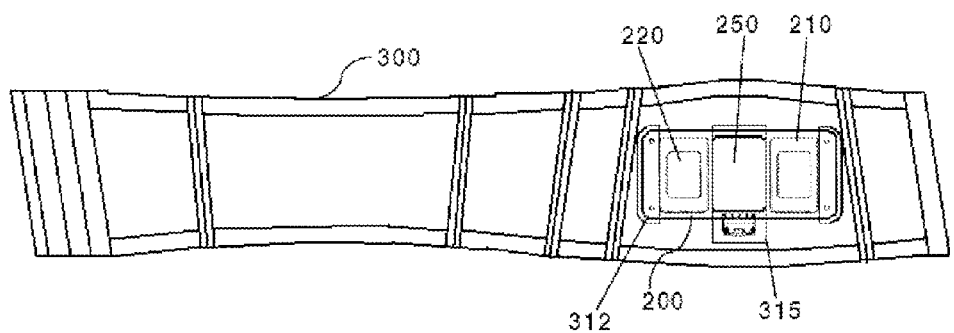
FIG. 8 is a view of a description of a construction that a menstrual pain alleviating part is engaged at a back side of a stomach warmer part of FIG. 7.

FIG. 7 is a rear side view of a stomach warmer part before a menstrual pain alleviating device is worn according to an embodiment of the present invention, and FIG. 8 is a view of a description of a construction that a menstrual pain alleviating part is engaged at a back side of a stomach warmer part of FIG. 7.

The stomach warmer part 300 is a means surrounded around the abdomen, thus more stably supporting the menstrual pain alleviating part 200 of the portable menstrual pain alleviating device. It can be fixed by just contacting the menstrual pain alleviating part 200 on a skin at usual time, but when there is a lot of movements of body, the stomach warmer part 300 helps more stably fix the menstrual pain alleviating part 200. Here, the stomach warmer part 300 includes a menstrual pain alleviating part engaging part 310.

The menstrual pain alleviating part engaging part 310 comprises a first menstrual pain alleviating part engaging part 312 and a second menstrual pain alleviating part engaging part 315 as a method for fixing the menstrual pain alleviating part 200 at a certain portion of the back side of the stomach warmer part 300.

The first menstrual pain alleviating part engaging part 312 might comprise a pocket (in a shape of pocket) formed at a certain position of the back surface of the stomach warmer part 300, in which pocket the left and right sides of the menstrual pain alleviating part 200 can be inserted, and might have a width enough for both left and right ends of the menstrual pain alleviating part 200 to be fixedly inserted, not being overlapped with the portion where the adhesion pad part 210 is positioned.

The second menstrual pain alleviating part engaging part 315 is a ring shaped means formed at a portion of the planar heater part 250 of the menstrual pain alleviating pat 200, into which ring-shaped means a center portion of the menstrual pain alleviating part 200 including the harness part 280. Both upper and lower sides of the second menstrual pain alleviating part engaging part 315 are closed when the stomach warmer 300 is worn, with the left and right sides being open. The size of the second menstrual pain alleviating part engaging part 315 might be changed, not being overlapped with the portion where the adhesion pad part 210 is positioned.

In case of the menstrual pain alleviating device body 100, it can be fixed at one side of the stomach warmer 300 or at a certain portion where the user wants to fix it.

It is obvious that the disclosures of the drawings and the detailed description of the present invention are not limited thereto, and those skilled in the art can easily amend or modify within the scope of the claims.

Industrial Applicability

The present invention is basically directed to a portable menstrual pain alleviating device with the aid of a TENS and warm heat stimulation. The portable menstrual pain alleviating device according to the present invention is easy to wear and is portable, so a user can use it any time anywhere, according to which women who are suffering from menstrual pains can have less pains due to menstrual pains while enhancing the quality of life and helping support women's social activities.

The invention claimed is:

1. A portable combined stimulation device for alleviating menstrual pain, which is directed to alleviating menstrual pains having a pain at a pubic area, comprising:
a menstrual pain alleviating part which includes a transcutaneous stimulation electrode pad part with a transcutaneous stimulation electrode for thereby providing an abdomen or a back portion with a transcutaneous stimulation, and a planar heater part with a planar heater for providing a warm heat stimulation to an abdomen; and
a menstrual pain alleviating device body which includes a power part for supplying electric power to the menstrual pain alleviating part, and a computation process part for generating a transcutaneous stimulation electrode control signal for controlling a transcutaneous stimulation electrode pad part and a planar heater control signal for controlling the planar heater part,
wherein the menstrual pain alleviating part comprises:
a circuit substrate part which includes a transcutaneous electrode circuit part at both left and right sides of the planar heater part for driving the transcutaneous stimulation electrode pad part, with the planar heater part being positioned at the center portion;
a circuit housing upper cover part which is positioned on the circuit substrate part and acts as an upper cover for covering the circuit substrate part and includes a transcutaneous stimulation electrode pad engaging part which is formed at a portion above the transcutaneous stimulation electrode circuit part of the circuit substrate part for engaging the transcutaneous stimulation electrode pad part;
a circuit housing lower cover part which is positioned below the circuit substrate part and acts as a lower cover for supporting the circuit substrate part and supports the circuit substrate part and is engaged with the circuit housing upper cover part; and
an adhesion pad part which is fixed at an upper surface of the circuit housing upper cover part and is positioned on the transcutaneous stimulation electrode pad engaged at the transcutaneous stimulation electrode pad and comes into contact with the skin as a patch type pad formed of a conductive gel.

2. A portable combined stimulation device for alleviating menstrual pain according to claim 1, wherein said power part comprises a rechargeable battery.

3. A portable combined stimulation device for alleviating menstrual pain according to claim 2, wherein said power part is charged by connecting a USB to a 220V commercial power, a notebook computer or a computer.

4. A portable combined stimulation device for alleviating menstrual pain according to claim 1, wherein said menstrual pain alleviating part comprises:
a temperature sensing part which includes a temperature sensor and detects the temperature of the planar heater part by engaging the temperature sensor at the planar heater body; and
an A/D conversion part for converting an output signal from the temperature sensing part into a digital signal.

5. A portable combined stimulation device for alleviating menstrual pain according to claim 4, wherein said computation process part controls the driving of the planar heater part to stop when the temperature detected by the temperature sensing part is higher than a previously set temperature of the planar heater part.

6. A portable combined stimulation device for alleviating menstrual pain according to claim 5, wherein said menstrual pain alleviating part body comprises:
- a key input part which includes an on/off switch of an operation of a menstrual pain alleviating device, a stimulation level setting mode part for setting the level of stimulation of the transcutaneous stimulation electrode pad part, a temperature setting mode part for setting the temperature of the planar heater, and an operation time setting mode part for setting the operation time of the transcutaneous stimulation electrode pad part and the planar heater;
- a display part which displays an output signal of the computation process part; and
- a D/A conversion part which converts an output signal from the computation process part into an analog signal.

7. A portable combined stimulation device for alleviating menstrual pain according to claim 6, further comprising:
- a transcutaneous stimulation electrode pad driving part which receives a transcutaneous stimulation electrode control signal from the computation process part via the D/A conversion part, thus driving the transcutaneous stimulation electrode pad; and
- a planar heater driving part which receives a planar heater control signal from the computation process part via the D/A conversion part, thus driving the planar heater part.

8. A portable combined stimulation device for alleviating menstrual pain according to claim 7, wherein a driving signal for driving the transcutaneous stimulation electrode pad at the transcutaneous stimulation electrode pad uses a bipolar square wave of a frequency of 100~120 Hz.

9. A portable combined stimulation device for alleviating menstrual pain according to claim 5, wherein when the temperature detected by the temperature sensing part is higher than a previously set temperature of the planar heater part, the state of which is informed by displaying or blinking a lamp or by using a vibrator to generate vibrations.

10. A portable combined stimulation device for alleviating menstrual pain according to claim 1, further comprising a stomach warmer to which said menstrual pain alleviating part is engaged.

11. A portable combined stimulation device for alleviating menstrual pain according to claim 10, wherein said stomach warmer includes a plurality of pockets into which left and right end portions of the menstrual pain alleviating part are fixedly inserted, with a ring being positioned at a center portion between neighboring pockets, with its upper and lower sides being closed, with its left and right sides being open, according to which the menstrual pain alleviating part is fixedly suspended over the ring.

12. A portable combined stimulation device for alleviating menstrual pain according to claim 1, wherein said transcutaneous stimulation electrode pad part is positioned to substantially cover the left and right sides of the front lateral collateral area and the anterior superior iliac spine of the left and right sides of the pubic (upper) portion at the abdomen.

13. A portable combined stimulation device for alleviating menstrual pain according to claim 1, wherein said transcutaneous stimulation electrode pad part is positioned to substantially cover the left and right sides of the back side including both lateral spinal cord portions of the spinal cord portion L3 of an inner side of a thigh and the spinal cord portion S2 level positioned at the perineum in the back portion.

14. A portable combined stimulation device for alleviating menstrual pain according to claim 1, wherein said planar heater is positioned at an abdominal portion including the Kwan-wan acupuncture point and the Seok-mum acupuncture point.

\* \* \* \* \*